(12) United States Patent
Baney et al.

(10) Patent No.: US 9,259,537 B2
(45) Date of Patent: Feb. 16, 2016

(54) INJECTION DEVICE WITH RETRACTABLE NEEDLE

(75) Inventors: Bruno Baney, Claix (FR); Frederic Perot, Saint Paul de Varces (FR); Kevin David Neale, Swindon (GB)

(73) Assignee: Becton Dickinson France S.A.S., Le Pont-de-Claix (FR)

(*) Notice: Subject to any disclaimer, the term of this patent is extended or adjusted under 35 U.S.C. 154(b) by 1752 days.

(21) Appl. No.: 12/298,647

(22) PCT Filed: Apr. 26, 2007
(Under 37 CFR 1.47)

(86) PCT No.: PCT/IB2007/001980
§ 371 (c)(1),
(2), (4) Date: May 5, 2010

(87) PCT Pub. No.: WO2007/125419
PCT Pub. Date: Nov. 8, 2007

(65) Prior Publication Data
US 2011/0015577 A1   Jan. 20, 2011

(30) Foreign Application Priority Data

Apr. 26, 2006 (FR) ...................... 06 03720

(51) Int. Cl.
*A61M 5/32* (2006.01)
*A61M 5/50* (2006.01)
(52) U.S. Cl.
CPC ............. *A61M 5/3234* (2013.01); *A61M 5/508* (2013.01)

(58) Field of Classification Search
CPC ...... A61M 5/32; A61M 5/3234; A61M 5/508
USPC ......................................... 604/192, 181, 187
See application file for complete search history.

(56) References Cited

U.S. PATENT DOCUMENTS

| 5,578,011 | A | 11/1996 | Shaw |
| 6,689,106 | B2 | 2/2004 | Bush et al. |

(Continued)

FOREIGN PATENT DOCUMENTS

| EP | 1421962 A | 5/2004 |
| JP | 10-272182 | 10/1998 |

(Continued)

*Primary Examiner* — Kami A Bosworth
*Assistant Examiner* — Brandy S Lee
(74) *Attorney, Agent, or Firm* — The Webb Law Firm (57) ABSTRACT

The present invention relates to a needle assembly (1) to be used in combination with a storing device (200) comprising a barrel (8) defining a chamber (9) receiving a product (4) and a piston (2), the assembly (1) comprising: —needle-bearing portion (7) in a first material, movable between an exposed and a retracted positions of the needle (5), —engaging means (8a, 10, 11, 18,) for securing said needle-bearing portion (7) to said barrel (8) in the exposed position, characterized in that it comprises: —sealing means (15) in a second material for tightly sealing the distal end (9a) of said chamber (9) to said needle-bearing portion (7), —a breakable portion (7a) located between said engaging means (8a, 10, 11, 18,) and said needle-bearing portion (7), which, when broken, allows independent proximal displacement of said needle-bearing portion (7) relative to said engaging means (8a, 10, 11, 18,) between said exposed and said retracted positions, said first material being more rigid than said second material. The invention also relates to an injection device (100) comprising said needle assembly (1) and a storing device (200).

42 Claims, 7 Drawing Sheets (56) References Cited

U.S. PATENT DOCUMENTS

2003/0163091 A1* 8/2003 Bush et al. .................. 604/181
2005/0159705 A1 7/2005 Crawford et al.
2006/0189935 A1 8/2006 Janek et al.

FOREIGN PATENT DOCUMENTS

| JP | 11-505454 | 5/1999 |
| WO | 96/35463 | 11/1996 |
| WO | 0162320 A1 | 8/2001 |

* cited by examiner

INJECTION DEVICE WITH RETRACTABLE NEEDLE

The present invention relates to a needle assembly for use in combination with a storing device, to an injection device comprising the needle assembly and a storing device, for example a syringe, and in particular a prefillable syringe, wherein the needle is retractable after use in order to avoid inadvertent exposure.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

People working in the medical field are confronted everyday to the use of syringes. Moreover, because of the risks associated with the contact of blood in general, it is of first importance for these people to have the safest working conditions. In particular, it is very important to prevent accidental pricking after completion of an injection to a patient.

A large number of syringes with different forms of safety devices, separate or integrated within the syringe body, have already been described and are present on the market. Syringes with separate safety devices are useful but they are bulky and may be difficult to handle. Syringes with retractable needles are particularly useful because they are compact and easy to manipulate.

One drawback of the syringes with current retractable needles is that they are not suitable for long time storage of product and have to be filled prior to injection. In order to realize an injection, one has to first draw the product from a vial and then to inject the product. Such operations are long and tedious and part of the dose of medicament to be administered may be lost in the process.

Such syringes are described in U.S. Pat. No. 6,689,106. The syringe described in this document comprises a needle hub, a piston and a hollow plunger rod in which the needle withdraws after some cutting surfaces provided in the needle hub have severed the needle from its hub and created a passage through the piston and in the hollow plunger rod. The integrated safety device of the syringe of U.S. Pat. No. 6,689,106 does not allow the prefilling of the syringe. The seal between the needle hub and the barrel is adapted to short-term storage between filling from a vial and injection. It is not adapted to long-term storage with risks of leakage and loss of drug by permeation through the hub. Additionally, the stopper is co-injected with the plunger rod, making it not adapted to conventional stopping process on automatic filling lines.

There is therefore a need for compact injection devices with retracting needles which would also allow the prefilling of the devices thanks to conventional filling processes and the long time storage of the products to be injected.

The present invention meets this need by providing a needle assembly usable in combination with a storing device and suitable as:
- long time storage container for any injection product when said needle assembly is used with a self standing piston, and
- compact injection device with a retractable needle when said needle assembly is used with a hollow plunger rod, and
- compatible with conventional filling processes thanks to a self standing piston.

In particular, as meant in the present application, a self standing piston is a piston capable of standing still on its own within the barrel of an injection device for instance, by friction of its side walls against the inner walls of said barrel, when no outside force is exerted on said piston. Such a self standing piston is compatible with conventional stoppering process on drug filling lines. It can be radially compressed and inserted in the syringe via a vent tube. The plunger rod can be mounted right after stoppering or in a later process step.

The present invention relates to a needle assembly intended to be used in combination with a storing device of a product, said storing device comprising at least:
- a barrel of substantially tubular shape having a distal end and a proximal end, said barrel defining a chamber for receiving said product,
- a piston intended to expel said product through the distal end under a distal force exerted on said piston, said needle assembly comprising at least:
- a needle-bearing portion, designed for receiving a needle and movable between an exposed position in which said needle is exposed and a retracted position in which the needle is hidden in said barrel, the said needle-bearing portion being born by a needle hub, said needle-hub and needle-bearing portion being made of a first material,
- engaging means, designed for securing said needle-bearing portion to said distal end of said barrel, at least in the exposed position, characterized in that it comprises:
- sealing means designed for tightly sealing the distal end of said chamber to said needle-bearing portion so as to avoid any leakage of said injectable product from the distal end of said chamber to the needle-bearing portion, at least in the exposed position, and reduce product permeation, said sealing means (15) being made of a second material,
- a breakable portion located between said engaging means and said needle-bearing portion, said breakable portion being arranged to, when broken, allow independent proximal displacement of said needle-bearing portion relative to said engaging means between said exposed and said retracted positions, said first material being more rigid than said second material.

In the present application, one means, by "breakable portion", that the portion may be separated, severed, broken, or cut or shread or split.

The needle assembly of the invention allows the providing of safe and compact injection devices. In particular, thanks to the needle assembly of the invention, it is possible to manufacture prefillable injection devices and to store therein drugs or injection products for a significant time, for instance up to three years, without deterioration of said drug and/or product. The injection device of the invention can therefore be used as a primary packaging for drug over long shelf life.

Because of the arrangement of the needle assembly of the invention, the stored product does not leak outside the storing device, the possible product permeation is reduced, and the product is not affected by water permeating through the needle assembly. The stored product is very stable over time.

Moreover, the injection device of the invention is safe: the needle is retracted within the barrel after use. Reuse of the injection device, as well as accidental pricking, are therefore prevented. The fact that the safety features of the injection device of the invention are integrated within the device, especially under the form of the barrel and/or the plunger rod that cover the needle after use, makes the whole prefillable device smaller and easier to manipulate for the user.

Additionally, the device of the invention is also easier to process for the pharmaceutical companies for example, during the filling and/or stoppering steps of standard processes.

In an embodiment of the invention, the sealing means comprise at least a plug at least partially made of a rubbery material. Preferably, the rubbery material is selected from the group comprising rubbers, thermoplastic elastomers, and any combination and analogs thereof. More preferably, the rubbery material is an olefin based thermoplastic elastomer. Such a material ensures an effective sealing between the chamber and the needle-bearing portion of the needle hub. In particular, the permeation of the product from the chamber to the outside is avoided. Preferably, the sealing means are deformable.

In an embodiment of the invention, the needle hub and the needle-bearing portion are made of a rigid material, for example a material having a hardness equal or more than 50 Shore D, and more preferably equal or more than 60 Shore D . . . . Preferably, the needle hub and the needle-bearing portion are at least partially made of a material selected from the group comprising rubbers, thermoplastic polymers such as polypropylene, polyethylene and any combination and analogs thereof. In an embodiment of the invention, the needle-hub and the needle bearing portion are made of polypropylene.

According to the invention, the material constituting the needle hub and the needle-bearing portion is more rigid than the material constituting the sealing means. For instance, the first material, constituting the needle hub and the needle bearing portion, shows preferably a hardness equal or more than 50 Shore D, and more preferably equal or more than 60 Shore D. The second material, constituting the sealing means, shows preferably a hardness ranging from 30 to 80 Shore A, and more preferably from 45 to 70 Shore A.

Thanks to the difference of hardness and rigidity between the first and the second materials, each function to be performed by each material, namely handling the needle on one side by the first material, and ensuring the sealing on the other side by the second material, is optimally performed by a material that has optimal characteristics to fulfil this function.

In an embodiment of the invention, the sealing means and the needle hub, including the needle-bearing portion, are physically linked to each other so as to avoid any leakage of product in-between their respective interfaces. Preferably, the sealing means and the needle hub, including the needle-bearing portion, are coinjected parts, preferably unitarily formed by coinjection. In such a case, product leakage and/or permeation are strongly avoided.

In a further embodiment of the invention, the breakable portion and the sealing means are combined.

In another embodiment of the invention, the engaging means and the sealing means are combined.

In a further embodiment of the invention, said sealing means are made of a material with a water permeation rate inferior or equal to 3 g·mm/m$^2$·day at room temperature, preferably inferior or equal to 1 g·mm/m$^2$·day at room temperature and more preferably inferior or equal to 0.5 g·mm/m$^2$·day at room temperature, measured according to the procedure "A" of the ASTM norm designation E 96-93. The water permeation rate is characterized by the water vapour transmission rate that is measured according to the designation E96-93 and more particularly the Procedure "A" corresponding to the desiccant method. In this desiccant method, the test specimen is sealed to the open mouth of a test dish containing a desiccant. The assembly is placed in a controlled atmosphere where the temperature is chosen between 21 and 32° C. (standard at 23° C.) and maintained constant within 0.6° C., and where the relative humidity is maintained at 50+/−2. Periodic weightings determine the rate of water vapour movement through the specimen into the desiccant.

In a further embodiment of the invention, at least said breakable portion is designed to be distally movable by said piston at the end of an injection stroke, and said needle assembly comprises severing means oriented toward said breakable portion and designed to be fixedly positioned compared to said needle-bearing portion in the exposed position, and arranged to break said breakable portion when it moves distally and then to allow proximal displacement of needle-bearing portion.

In a further embodiment of the invention, the engaging means comprise a radial wall portion designed to be snapped in an annular groove at least partly formed on said barrel, in the exposed position. Alternatively, the barrel may comprise a radial wall portion designed to be snapped in an annular groove of the engaging means.

In an embodiment of the invention, said radial wall portion is made of a deformable material.

In an embodiment of the invention, the radial wall portion is a flange defined on the needle hub.

In another embodiment of the invention, said radial wall portion is a plurality of radial projections defined on the needle hub. For example, the radial projections may form the distal and/or the proximal ends of a plurality of longitudinal flexible legs extending respectively in the distal and/or the proximal, direction.

In an embodiment of the invention, said sealing means comprise a longitudinal skirt extending in the distal, respectively the proximal, direction, said skirt receiving part of the proximal region of said needle hub and being fixedly received in said distal end of said barrel. Preferably, said skirt is able to fold back on itself from the exposed position to an activation position. In the activation position, preferably, the skirt, by creating a soft resistance to the distal movement of the breakable portion, allows the control of the cut of said breakable portion by the severing means. In particular, the necessary force to cut the breakable portion must be high enough to prevent premature activation of the severing means.

In a further embodiment of the invention, the severing means comprise at least cutting surfaces designed at the proximal end of a sleeve receiving part of the needle-bearing portion of said needle hub.

The needle assembly of the invention may comprise urging means placed between said engaging means and said needle-bearing portion and designed to tend to move said needle-bearing portion apart from said engaging means in the proximal direction. For example, said urging means may be a helical spring.

The needle assembly of the invention may further comprises a nose designed to be adapted at the distal end of the barrel and to receive, at least in the exposed position, said needle-bearing portion, said breakable portion and said sealing means.

In an embodiment of the invention, the needle assembly further comprises a needle. The needle assembly of the invention may further comprise a needle cover. The needle cover preferably comprises a rubber plug that maintains the sterility of the needle and prevents product leakage from the chamber and through the passage way defined by the needle.

The present invention also relates to an injection device of a product, comprising at least a storing device and characterized in that it comprises a needle assembly as described above.

In a preferred embodiment of the invention, said storing device comprises at least:

a barrel of substantially tubular shape having a distal end and a proximal end, said barrel defining a chamber for receiving said product, a piston intended to expel said product through the distal end under a distal force exerted on said piston, said storing device being prefillable with said product and said piston sealing the proximal end of said barrel.

Preferably, said piston is a self standing piston. The device of the invention may then be used as a storage device for the product. Moreover, such a piston is compatible with conventional stoppering process on product filling lines at pharmaceutical companies. For example, the self standing piston can be radially compressed and inserted in the barrel via a vent tube. A plunger rod may be added right after this stoppering step or later.

In an embodiment of the invention, the barrel comprises an annular groove defining on its inner wall an abutment designed to receive said radial wall portion of the needle-bearing portion at least in the exposed position. Preferably, the abutment is an annular ridge.

Alternatively, the barrel may comprise an annular groove defining on its inner wall an abutment designed to receive a radial wall portion designed on the needle-bearing portion, at least in the exposed position. The abutment is for example an annular ridge.

In a further embodiment of the invention, said barrel is made of a material selected from the group comprising polypropylene, polycycloolefins, and combinations thereof. The barrel can also be made of glass or any other suitable material.

In a further embodiment of the invention, the injection device comprises a storing device and driven means for causing said piston to move toward the distal end of said needle assembly and realize the injection of the product. Preferably, said driven means comprise a hollow plunger rod designed to receive at least said needle in its retracted position.

In an embodiment of the invention, the distal end of said plunger rod is at least partially open.

In a further embodiment of the invention, the distal end of said plunger rod comprises supporting means, designed to form a radial bearing surface for the piston to prevent said piston from deforming itself in said plunger rod as the severing means cut said piston under the effect of the distal force exerted on said plunger rod at the end of injection. The supporting means also provide a clean cut of the piston and therefore a good passage through for the needle.

Preferably, the supporting means comprise a radial wall portion. For example, the radial wall portion may define a plurality of radial extensions.

In a preferred embodiment of the invention, said piston is made of a rubbery material.

Preferably, said piston is made of a material with a water permeation rate inferior or equal to 3 g·mm/m²·day at room temperature, preferably inferior or equal to 1 g·mm/m²·day at room temperature and more preferably inferior or equal to 0.5 g·mm/m²·day at room temperature, measured according to the procedure "A" of the ASTM norm designation E 96-93.

Such a piston prevents leakage of the injection product to the outside and contamination of the stored injection product.

The present invention will now be described in greater detail with the aid of the attached drawings in which.

Figure 1:
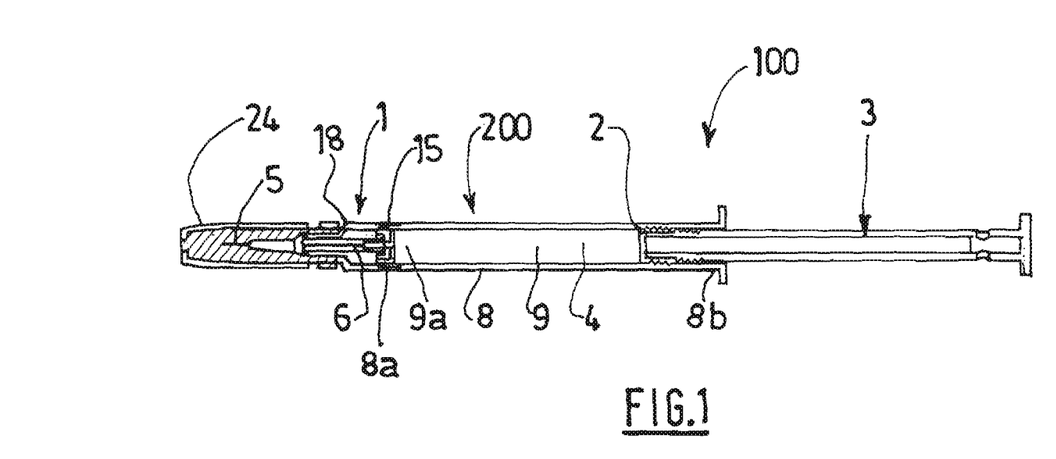
FIG. 1 is a side view of an injection device according to the invention.

In reference to FIG. 1, is shown an injection device 100 according to the invention comprising a storing device 200 and a needle assembly 1 according to the invention. The storing device 200 comprises a barrel 8 having a substantially tubular shape. The barrel 8 may be made of a material selected from the group comprising polypropylene, polycycloolefins and/or combinations thereof. Such materials are preferred since they are compatible with long term product storage. Moreover, they usually are transparent and therefore allow a good visual evaluation of the quantity and quality of product stored.

The barrel 8 has a distal end 8a and a proximal end 8b and it defines a chamber 9 which receives a product 4. The product 4 may be any product that is suitable for an injection to a patient, such as a medicine. Preferably, the product 4 is stored within the storing device 200 before it is injected.

The injection device 100 of FIG. 1 also comprises a piston 2 which is intended to expel the product 4 through the distal end 8a of the barrel 8 under a distal force exerted on said piston 2 and movement of the piston 2 along an injection stroke, for example in order to inject the product 4. In this view, the piston 2 of the injection device 100 of FIG. 1 is fixed, for instance by screwing, to the distal end of a hollow plunger rod 3 which can be manually driven for causing said piston 2 to move in the distal direction in order to inject the product 4.

Alternatively, in an embodiment of the invention not shown, the piston 2 could be snapped on the distal end of the plunger rod 3.

As appears from the position shown on FIG. 1, the storing device 200 may be prefilled with the product 4 and the piston 2 seals the proximal end 8b of the barrel 8.

In an embodiment not shown the piston 2 is a self standing piston. In other words, in such an embodiment, the piston 2 is on its own and is not linked to any driven means such as a plunger rod. Preferably, the self standing piston 2 is deformable and it may be inserted in the barrel 8 by means of a vent tube (not shown), that radially compresses it. Once it is introduced in the barrel 8 and exits the vent tube, the radial pressure is released and the self standing piston 2 expands until it stands naturally still by friction of its side faces against the inner walls of the barrel 8. In such a position, the self standing piston 2 seals the proximal end 8b of the barrel 8 and the product 4 may be stored this way for some time.

As the injection device 100 is dedicated to long term storage of product 4, it is important that all interfaces be impermeable to prevent any loss of product 4 overtime and/or product 4 alteration. In particular, it is preferable that the piston 2, whether it be self standing or not, be made from a material with a low water permeation rate expressed and characterized by the water vapour transmission rate that is measured according to the ASTM norm designation E96-93. The material can be a rubbery material and is preferably selected from the halobutyl rubbers. Halobutyl rubbers are rubbery materials which present a low water permeation rate and they contribute to a better stability of the stored product over time. Moreover, it is also preferable that the piston 2 be made of a material with a water permeation rate inferior or equal to 3 g·mm/m²·day at room temperature, preferably inferior or equal to 1 g·mm/m²·day at room temperature and more preferably inferior or equal to 0.5 g·mm/m²·day at room temperature. The piston 2 therefore prevents the permeation of water vapour outside.

Such a piston 2 made of such a material is also very effective in preventing any leakage of product 4 outside the barrel 8.

The features of the needle assembly 1 of the injection device 100 of FIG. 1 appear more clearly on FIGS. 2 to 5 which show the relative positions of the elements composing said needle assembly 1 when the injection device 100 is in use from a storage position to an end-of-use position when the injection device 100 may be disposed.

Figure 14:
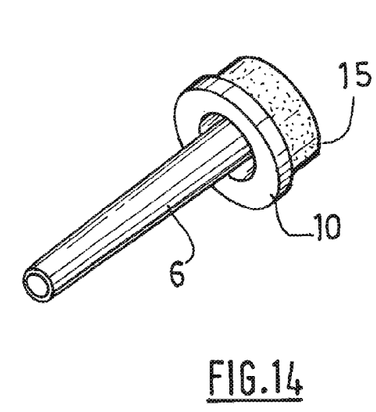
FIG. 14 is a perspective view of the needle hub and the sealing means of the needle assembly of the device of FIGS. 1-5.

As shown on these figures, the needle assembly 1 comprises a needle hub 6. On the example shown, this needle hub 6 has a needle-bearing portion 7, under the form of a tube receiving the needle 5, and a radial wall portion, under the form of a flange 10, linked to the proximal end of the tube receiving the needle 5 by means of a breakable portion 7a, the use of which will be explained later. The flange 10 of the needle hub 6 of FIGS. 1-5 appears more clearly on FIG. 14 which is a perspective view of said needle hub 6 together with the sealings means 15 described hereinbelow.

Figure 15:
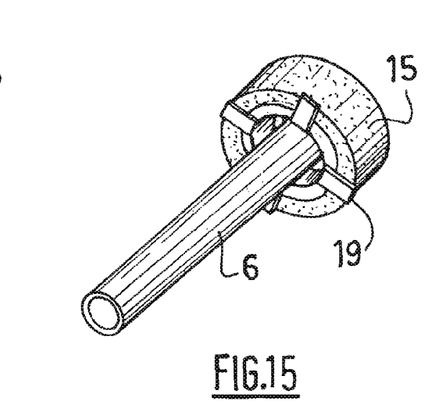
FIG. 15 is a perspective view of a variant of the needle hub of FIG. 14.

Alternatively, the radial wall portion of the needle hub 6 may be under the form of a plurality, four on the example shown on FIG. 15, of radial projections 19.

Preferably, the needle hub 6 is at least partially made of a rigid material. For instance, the needle hub 6 is made of a material selected from the group comprising rubbers, thermoplastic polymers such as polypropylene, polyethylene and analogs thereof. In the example shown on FIGS. 2-5, the needle hub 6, as well as the needle-bearing portion 7, are made of polypropylene and show a hardness equal or more than 50 Shore D.

As shown on FIGS. 2 to 5, the needle assembly 1 also comprises a sealing means, under the form of a plug 15 in the example shown, designed for tightly sealing the distal end 9a of the chamber 9 to the needle-bearing portion 7 of the needle-hub 6. Preferably, the plug 15 is deformable and made of a rubbery material, and more preferably said rubbery material is selected from the group comprising rubbers, thermoplastic elastomers, any combination and analogs thereof. In the example shown, the plug 15 is made of an olefin based thermoplastic elastomer and it shows a hardness ranging from 30 to 80 Shore A.

The needle hub 6, including the needle-bearing portion 7, and the plug 15 are therefore made of two different materials having different hardness and rigidity characteristics. In particular, the hardness and rigidity of the first material, constituting the needle hub 6 and the needle-bearing portion 7, is higher than the hardness and rigidity of the second material, constituting the plug 15. This difference of hardness and rigidity characteristics allows each element, the needle bearing portion 7 on one side and the plug 15 on the other side to perform its own function in an optimal way.

Figure 2:
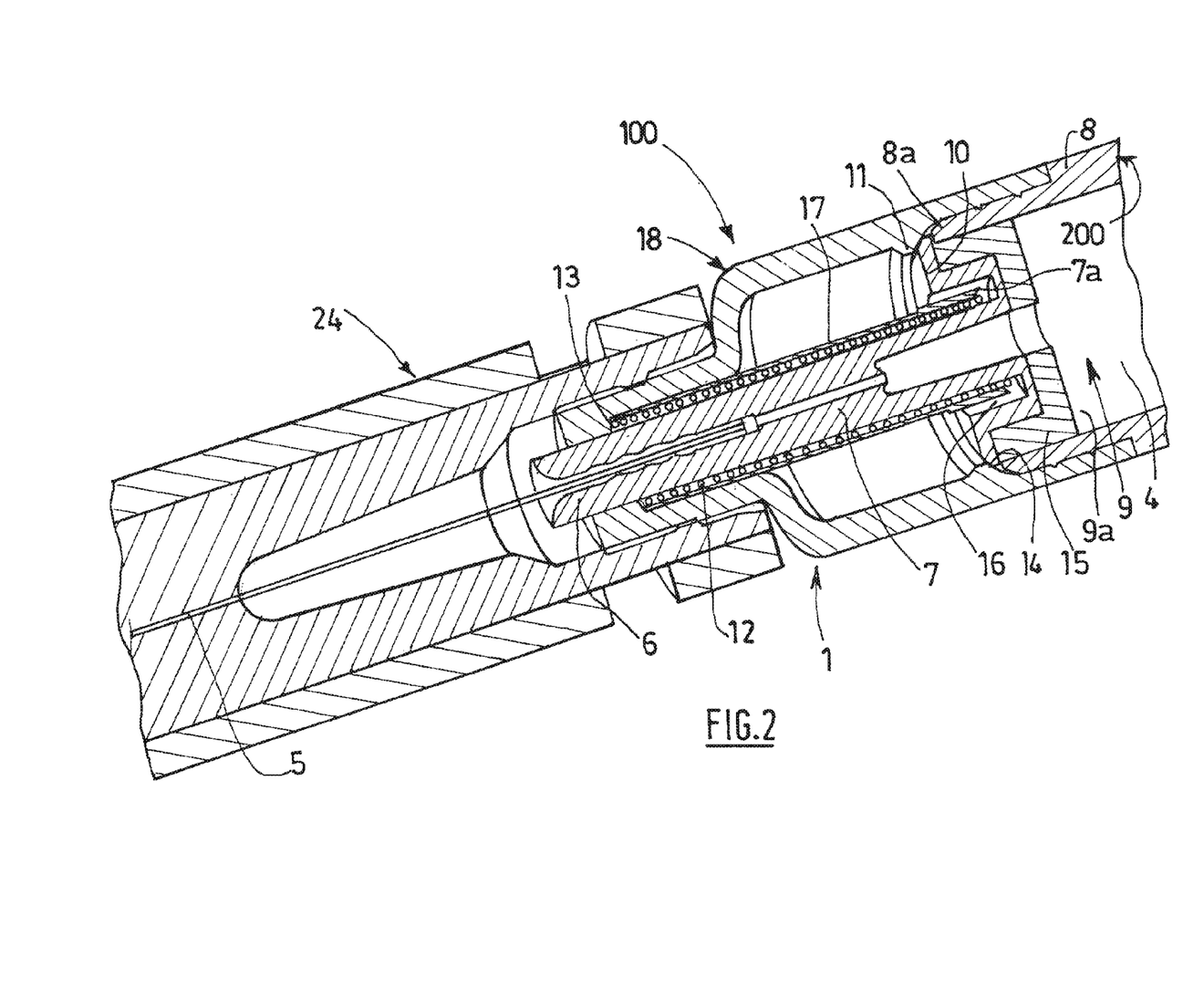
FIG. 2 is a view in section of a needle assembly of the invention.

The sealing means 15 of needle assembly of the invention allows to avoid the leakage of the injection product 4 from the distal end 9a of the chamber 9 in which said product 4 is stored in the exposed position, as shown on FIG. 2, to the needle-bearing portion 7. This sealing means 15 therefore reduces product 4 permeation. Additionally, the sealing means 15 allows to prevent contamination from the outside to the product 4 in the chamber 9.

Preferably, the sealing means 15 is made of a material with a water permeation rate inferior or equal to 3 g·mm/m²·day at room temperature, preferably inferior or equal to 1 g·mm/m²·day at room temperature and more preferably inferior or equal to 0.5 g·mm/m²·day at room temperature. Such a sealing means 15 allows therefore the long term storage of the product 4. Moreover, thanks to the presence of this sealing means and to its nature, the product 4 may be stored for a long term with an excellent stability.

Preferably, the sealing means 15 and the needle hub 6 are physically linked to each other so as to avoid any leakage of product 4 in-between their respective interfaces. For instance, in the example shown on FIGS. 2-5, the plug 15 and the needle hub 6 are coinjected parts. The leakage of the product 4 at the interfaces of the two parts, that is to say the plug 15 on one hand, and the needle hub 6 on the other hand is therefore avoided.

As shown on FIGS. 2 to 5, the needle assembly 1 also comprises a nose 18 which is adapted at the distal end 8a of the barrel 8. This nose 18 receives, in the exposed position of the needle 5 as shown on FIGS. 2 to 4, the needle-bearing portion 7, the breakable portion 7a and the sealing means 15. The nose 18 comprises, on its inner wall, an annular ridge 11 forming an abutment. This annular ridge 11 forms, together with the distal end 8a of the barrel 8, an annular groove 14 in which the flange 10 of the needle hub 6 is snapped, in the exposed position as shown on FIGS. 2 and 3. The distal end 8a of the barrel 8, the flange 10 of the needle hub 6, the nose 18 and its annular ridge 11 therefore form altogether engaging means designed for securing the needle hub 6 to the distal end 8a of the barrel 8 in the exposed position.

Alternatively, in an embodiment of the invention not shown, the barrel 8 may comprise a radial wall portion designed to be snapped in an annular groove of the engaging means. For instance, the needle hub 6 may comprise an annular groove defining on its inner wall an abutment designed to receive a radial wall portion designed on the inner wall of the barrel 8. Such an embodiment also ensures the securing of the needle hub 6 to the distal end 8a of the barrel 8 in the exposed position.

As appears from FIG. 2, the breakable portion 7a of the needle hub 6 is located between the engaging means 8a, 10, 11, 18 and the needle-bearing portion 7. This needle-bearing portion 7 is movable between the exposed position of the needle 5, shown on FIGS. 2 and 3 and the retracted position, shown on FIG. 5, in which said needle 5 is hidden in the barrel 8. The breakable portion 7a is arranged to, when broken, allow independent proximal displacement of said needle-bearing portion 7 relative to said engaging means 8a, 10, 11, 18 between said exposed and said retracted positions of the needle 5.

In an embodiment of the invention not shown, the breakable portion 7a and the sealing means 15 are combined, ie they form one single element, yet having different hardness and rigidity characteristics.

The needle assembly 1 of FIGS. 2-5 further comprises a sleeve 17 which receives the tube receiving the needle 5 of the needle-bearing portion 7 of the needle hub 6. This sleeve 17 comprises at its proximal end cutting surfaces 16 which are oriented toward the breakable portion 7a and designed to be fixedly positioned compared to said needle-bearing portion 7 in the exposed position. These cutting surfaces 16 form severing means of the breakable portion 7a.

As shown on FIGS. 2 to 5, a helical spring 12 is located between the sleeve 17 and the needle-bearing portion 7, the proximal end of said spring 12 bearing on the breakable portion 7a and the distal end of said spring 12 bearing on a radial stop 13 defined on the inner wall of the distal region of the nose 18.

The use of the device 100 of the invention will now be explained in reference to FIGS. 1 to 5.

The user is provided with the device 100 of the invention as shown on FIGS. 1 and 2, in the storing position: in this position, the needle assembly 1 of the invention described above comprises a needle 5 which is in the exposed position. Preferably, in order to avoid any accidental pricking, the needle assembly 1 further comprises a needle cover 24 in order to protect the needle 5. The needle cover 24 preferably comprises a rubber plug that maintains the sterility of the needle 5 and prevents product 4 leakage from the chamber 9 and through the passage way defined by the needle 5. In this position, the spring 12 is in a compressed state and it therefore constitutes urging means placed between the engaging means 8a, 10, 11, 18 and the needle-bearing portion 7 and designed to tend to move said needle-bearing portion 7 apart from said engaging means 8a, 10, 11, 18 in the proximal direction: in the position shown on FIGS. 1 and 2 though, this urging means is not activated.

The user removes the needle cover 24 and proceeds to the injection phase by exerting a distal force on the plunger rod 3 so as to cause the piston 2 to move toward the distal end of the needle assembly 1 and realize the injection of the product 4.

Figures 3, 4:
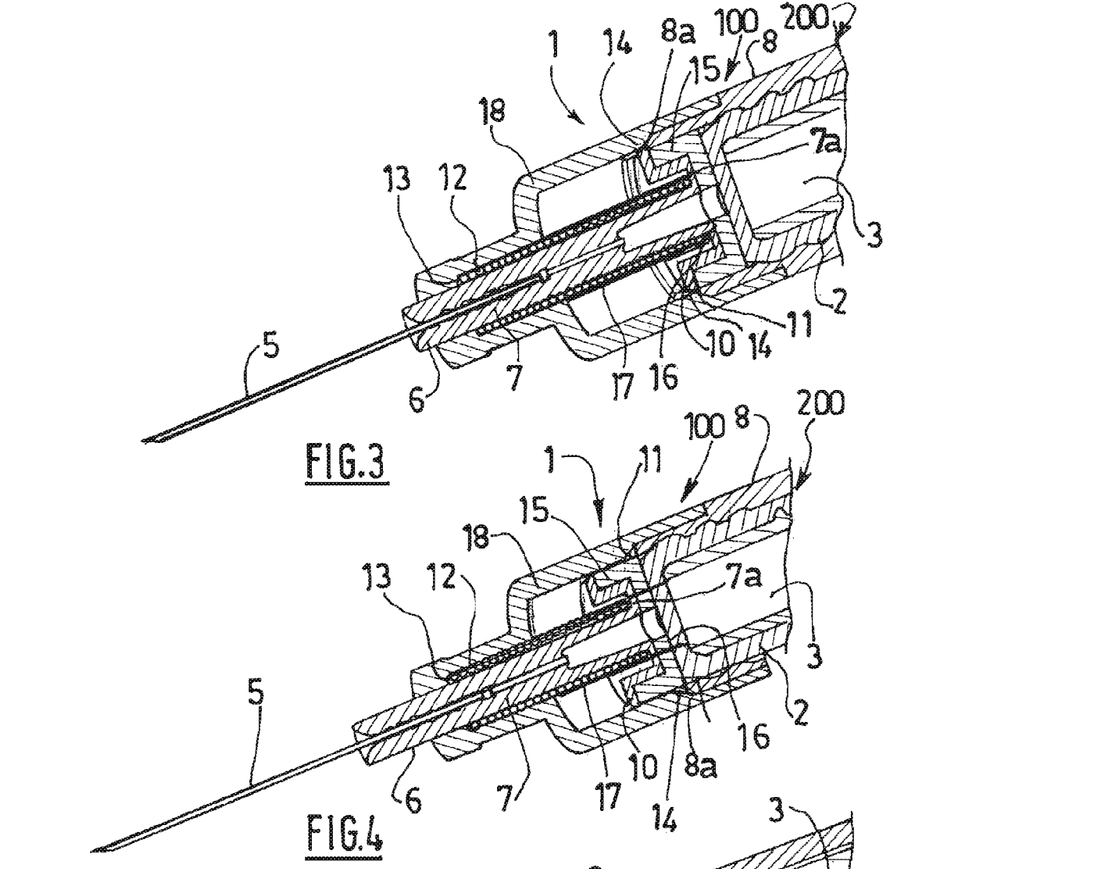
FIG. 3 is a partial view in section of the injection device of the invention, in the exposed position.
FIG. 4 is a view in section of the injection device of FIG. 3 at the end of injection, showing how the severing means operate.
Figure 5:
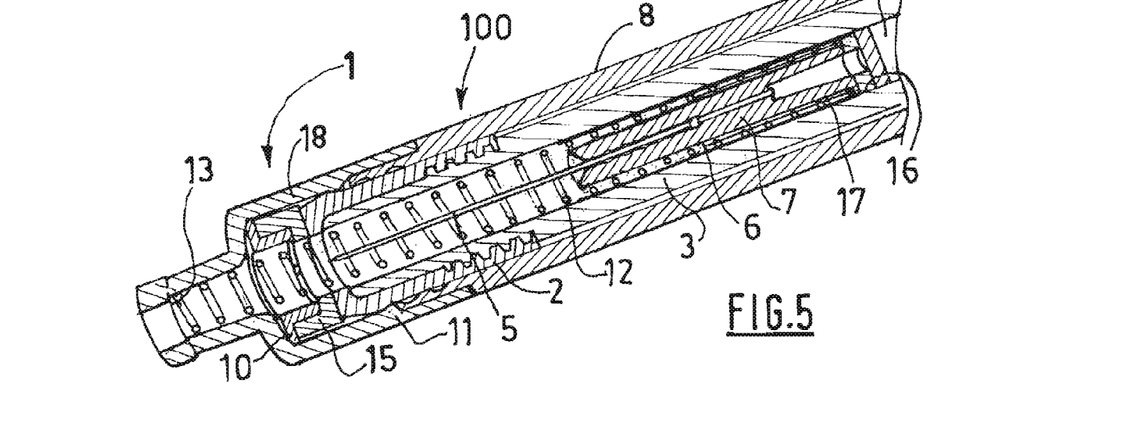
FIG. 5 is a view in section of the injection device of FIGS. 3 and 4 in the retracted position.

At the end of injection, the piston 2 comes in contact with the plug 15 as shown on FIG. 3. The breakable portion 7a is designed to be distally movable by the piston 2 at the end of injection, in particular under the effect of an additional distal force exerted on said piston 2 at the end of injection. This additional force is necessary for disengaging the flange 10 of the needle hub 6 from the engaging means 8a, 11 and allowing the distal displacement of the breakable portion 7a. This additional force is high enough to prevent premature activation of the severing means 16. It is to be noted that the engaging means 8a, 10, 11, 18 are designed to prevent any premature activation of the system upon pressure build up inside the chamber 9. They are also set to provide acceptable, ie sufficient enough but not too high, force to activate the safety system described herein.

The user therefore pushes further on the plunger rod 3, causing the piston 2 to move distally the breakable portion 7a until said breakable portion 7a comes in contact with the cutting surfaces 16 of the sleeve 17. The cutting surfaces 16 act as severing means which break the breakable portion 7a as said breakable portion 7a moves distally, as shown on FIG. 4. On further distal force exerted on the plunger rod 3 and therefore on the piston 2, the sealing means, ie the plug 15, and then the piston 2 itself are successively cut by the cutting surfaces 16 as shown on FIG. 4. Therefore, once broken, the breakable portion 7a allows the independent proximal displacement of the barrel 8.

The proximal end of the spring 12 is by way of consequence no more retained by the breakable portion 7a and said spring 12 then aims at returning to its rest position: it expands in the proximal direction, drawing with him the needle-bearing portion 7 and the needle 5. The needle 5 is therefore drawn together with the needle-bearing portion 7 inside the plunger rod 3 as shown on FIG. 5. The needle 5 is eventually in the retracted position. In this position, the device 100 is safe. The needle 5 is no more exposed and accidental pricking is prevented. The injection device 100 may be disposed.

Figure 6:
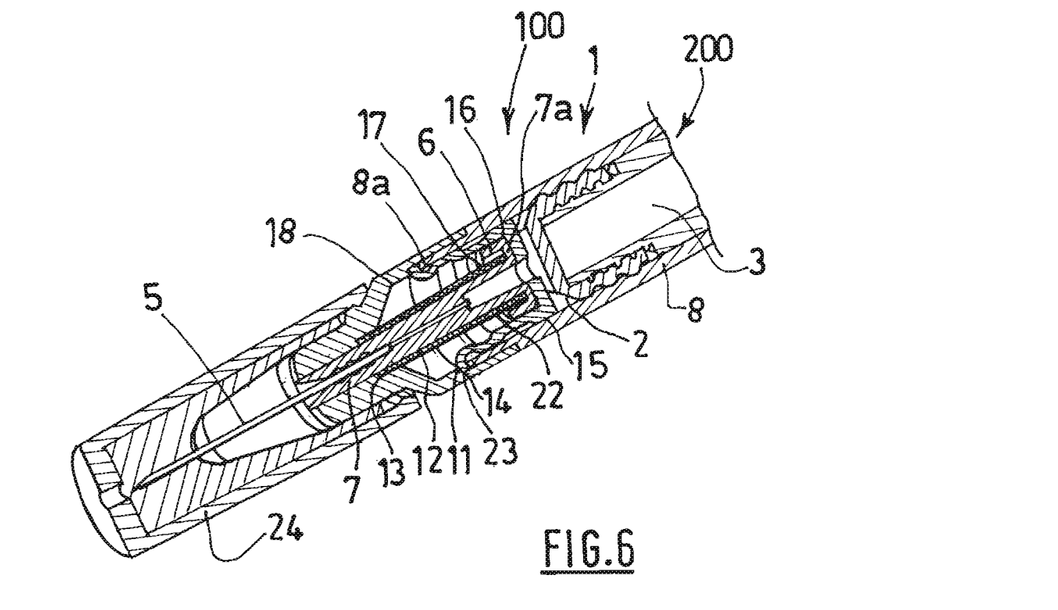
FIG. 6 is a partial view in section of a variant of the injection device of the invention, in the exposed position.
Figure 7:
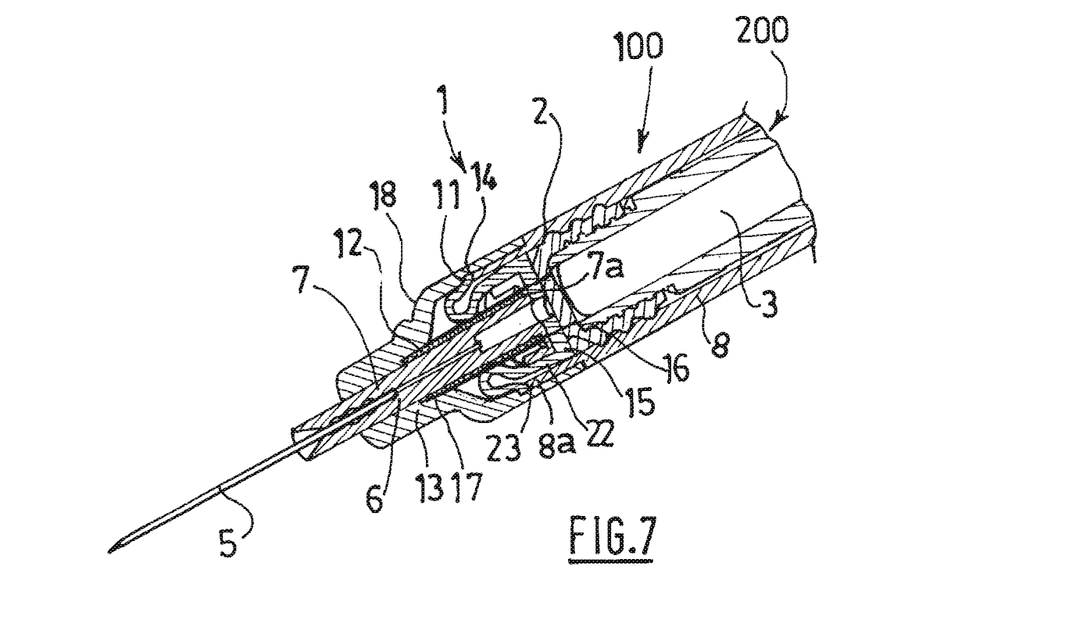
FIG. 7 is a view in section of the device of FIG. 6, showing how the severing means operate.

On FIGS. 6 and 7 is shown a variant of the needle assembly 1 shown on FIGS. 1 to 5, in which the sealing means 15 comprise a longitudinal skirt 22 extending in the distal direction. The references designating the same elements as in FIGS. 1-5 have been maintained.

As can be seen on FIG. 6, the skirt 22 receives part of the proximal region of the needle hub 6 and it is designed to fixedly being received in the distal end 8a of the barrel 8. In particular, the skirt 22 comprises at its distal end a radial wall portion 23 which, in the exposed position shown on FIG. 6, is snapped in an annular groove 14 formed by the distal end 8a of the barrel and an annular ridge 11 defined on the inner wall of the nose 18. The radial wall portion 23, the distal end 8a of the barrel 8, the annular ridge 11 and the nose 18 therefore form engaging means that secure the needle hub 6 to the distal end 8a of the barrel 8 in the exposed position. In such an embodiment, part of the engaging means and the sealing means are combined.

The skirt 22 and its radial wall portion 23 are made of a deformable material. The skirt 22 is therefore able to fold back on itself from the exposed position shown on FIG. 6 to an activation position, or cutting position, shown on FIG. 7. In this position, the piston 2, under the effect of a distal force exerted on the plunger rod 3, has moved distally the breakable portion 7a of the needle hub 6 until it is in contact with the cutting surfaces 16 of the sleeve 17. During this distal displacement of the breakable portion, the skirt 22 has started to fold back on itself, providing a soft friction force for the user to overcome while exerting a distal force on the plunger rod 3 and in consequence providing a damping of said distal force allowing a better control of the displacement of the piston 2. Under further distal pressure on the piston 2, the cutting surfaces 16 sever the breakable portion 7a, then cut the sealing means 15 and finally the piston 2, while the skirt 22 completely folds back on itself as shown on FIG. 7.

The final position, following the one shown on FIG. 7 is not shown. It corresponds to the retracted position, where the needle 5 is hidden within the plunger rod 3 after the spring 12 has returned to its rest position, drawing with him the needle-bearing portion 7 and the needle 5 in the proximal direction.

In an alternative embodiment of the invention not shown, the skirt 22 may extend in the proximal direction.

Figure 8:
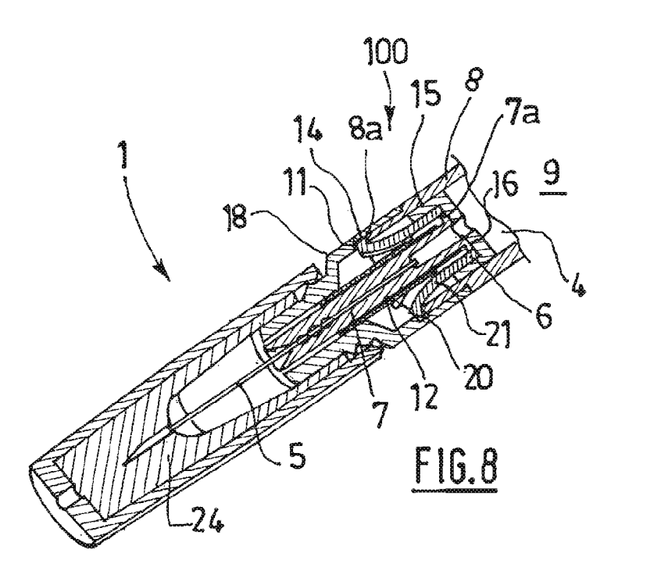
FIG. 8 is a partial view in section of another variant of the injection device of the invention, in the exposed position.
Figure 9:
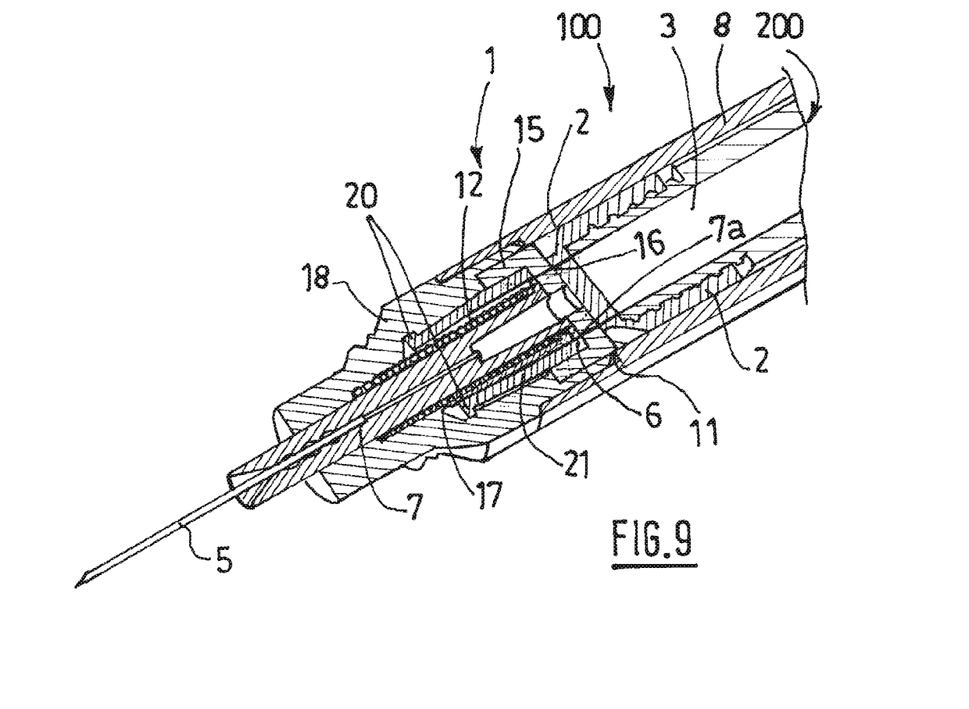
FIG. 9 is a view in section of the device of FIG. 8, showing how the severing means operate.
Figure 10:
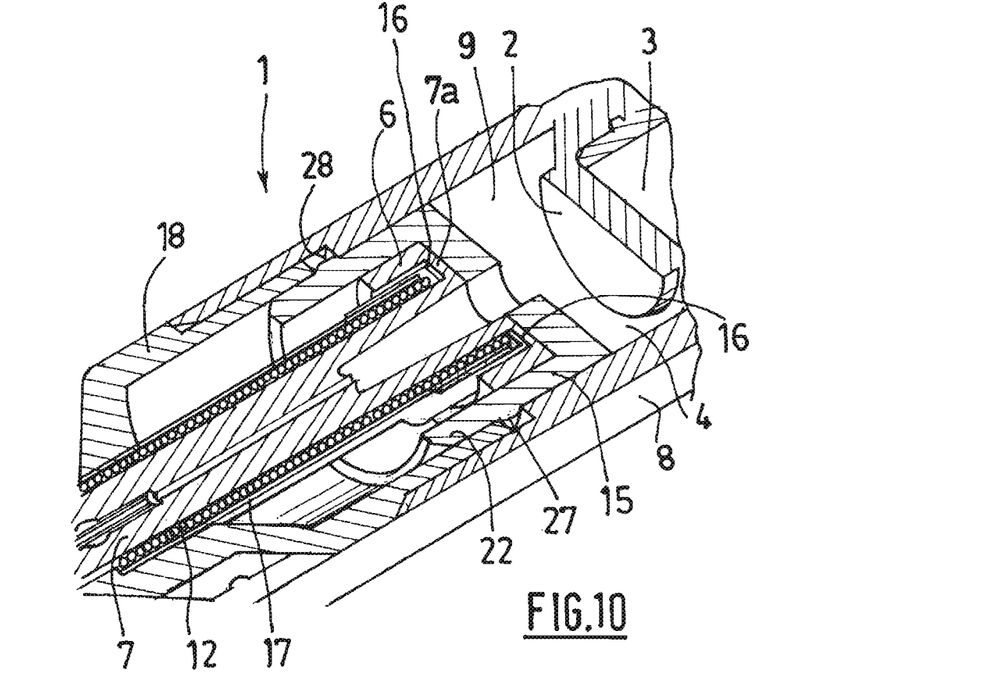
FIG. 10 is a partial view in section of another variant of the injection device of the invention.
Figure 11:
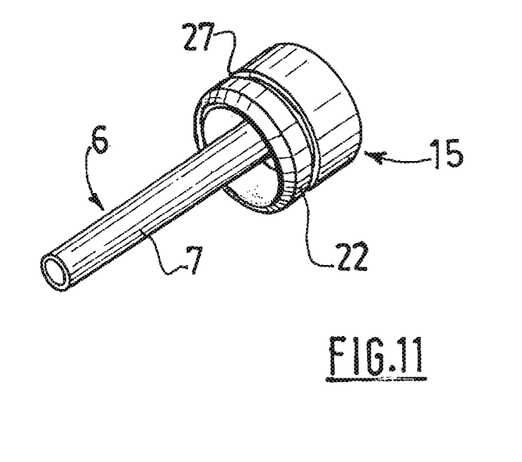
FIG. 11 is a perspective view of the needle hub and sealing means of the device of FIG. 10.

On FIGS. 10 and 11 is shown a variant of the embodiment of FIGS. 6 and 7, wherein the skirt 22 does not fold back on itself but is provided, on its outer wall, with an annular projection 27 which, in the exposed position, as shown on FIG. 10, is snapped between the proximal end of the nose 18 and an abutment 28 defined on the inner wall of the barrel 8. The references designating the same elements as in FIGS. 1-7 have been maintained On FIGS. 8 and 9 is shown a variant of the needle assembly 1 of the invention, wherein the engaging means comprise a radial wall portion designed to be snapped in an annular groove 14 at least partly defined by the barrel 8, in the exposed position, said radial wall portion being a plurality of radial projections defined on the needle hub 6 and where the radial projections form the distal ends 20 of a plurality of longitudinal flexible legs 21 extending in the distal direction. The references designating the same elements as in FIGS. 1-5 have been maintained.

Alternatively, in an embodiment of the invention not shown, the radial projections form the proximal ends of a plurality of longitudinal flexible legs extending in the proximal direction.

As can be seen from FIGS. 8 and 9, the ends 20 are made of a deformable material. In the exposed position, shown on FIG. 8, the ends 20 are snapped in an annular groove 14 formed by an annular ridge 11 defined on said nose 18 and the distal end 8a of the barrel 8. The ends 20, the annular ridge 11, the distal end 8a of the barrel 8 and the nose 18 therefore form engaging means that secure the needle hub 6 to the distal end 8a of the barrel 8 in the exposed position.

The FIG. 9 shows the embodiment of FIG. 8 in the cutting position, once the ends 20 of the longitudinal flexible legs 21 have overcome the annular ridge 11 under the distal pressure of the piston 2 pushed distally by the distal force exerted by the user on the plunger rod 3.

The cutting surfaces 16 of the sleeve 17 then break the breakable portion 7a, cut the sealing means 15 and the piston 2.

The needle 5 is then drawn within the plunger rod 3 by action of the spring 12 which returns to its rest position, as described in the previous embodiments above.

Figure 12:
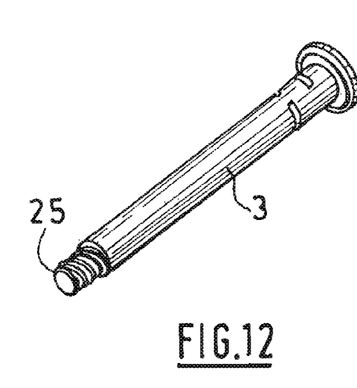
FIG. 12 is a perspective view of a plunger rod of an injection device of the invention.

On FIG. 12 is shown a plunger rod 3 suitable as a driven means for causing the piston 2 of the injection devices 100 of FIGS. 1-11 to move toward the distal end of the needle assembly 1 of said injection device 100 and inject the product 4. On this figure, the plunger rod 3 is hollow and designed to receive the needle 5 in the retracted position, as already shown for instance on FIG. 5. To this view, the distal end 25 of said plunger rod 3 is open.

Figure 13:
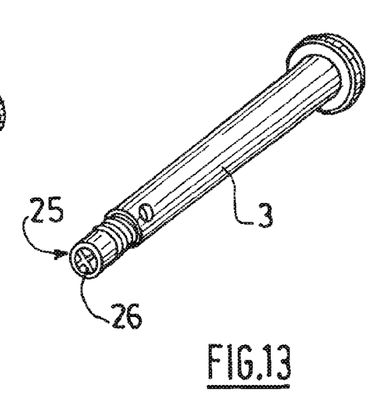
FIG. 13 is a perspective view of a variant of the plunger rod of FIG. 12.

On FIG. 13, is shown a variant of the hollow plunger rod 3 of FIG. 12, wherein the distal end 25 of said plunger rod 3 comprises supporting means designed to form a radial bearing surface for the piston 2 to prevent said piston 2 from deforming itself in said plunger rod 3 as the severing means 16 cut said piston 2 under the effect of the distal force exerted on said plunger rod 3 at the end of injection. The supporting means also help providing a clean cut of the piston 2 and therefore a good passage through for the needle 5. On the example shown on FIG. 13, the supporting means comprise a radial wall portion 26, which, on this example, defines a plurality of radial extensions forming a cross. After having cut the breakable portion 7a, the sealing means 15 and the piston 2, the cutting surfaces 16 of the severing means also cut these radial extensions and the needle 5 is allowed to withdraw within the plunger rod 3.

The needle assembly 1 of the invention allows the manufacture of prefillable injection devices 100 with an integrated safety system. The injection devices 100 of the invention are therefore safe, compact and easy to handle, both as a final product by the end-users, such as nurses, and as a manufacturing product by the pharmaceutical companies for instance, during the filling and/or stoppering processes.

The invention claimed is:

1. Needle assembly intended to be used in combination with a storing device of a product, said storing device comprising at least:
   a barrel of substantially tubular shape having a distal end and a proximal end, said barrel defining a chamber for receiving said product, and
   a piston intended to expel said product through the distal end under a distal force exerted on said piston,
   said needle assembly comprising at least:
   a needle-bearing portion, designed for receiving a needle and movable between an exposed position in which said needle is exposed and a retracted position in which the needle is hidden in said barrel, the said needle-bearing portion being borne by a needle hub, said needle hub and needle-bearing portion being made of a first material,
   engaging means, designed for securing said needle-bearing portion to said distal end of said barrel, at least in the exposed position,
   sealing means fixed at the distal end of the chamber for tightly sealing the distal end of said chamber to said needle-bearing portion so as to avoid any leakage of said injectable product from the distal end of said chamber to the needle-bearing portion, at least in the exposed position, and reduce product permeation, said sealing means being made of a second material, and
   a breakable portion located between said engaging means and said needle-bearing portion, said breakable portion being arranged to, when broken, allow independent proximal displacement of said needle-bearing portion relative to said engaging means between said exposed and said retracted positions,
   wherein said first material being more rigid than said second material, and
   wherein said sealing means is located between the chamber and the breakable portion prior to the breakable portion being broken.

2. Needle assembly according to claim 1, wherein said first material shows a hardness equal or more than 50 Shore D.

3. Needle assembly according to claim 2, wherein said hardness is equal or more than 60 Shore D.

4. Needle assembly according to claim 1, wherein said second material shows a hardness ranging from 30 to 80 Shore A.

5. Needle assembly according to claim 4, wherein said hardness ranges from 45 to 70 Shore A.

6. Needle assembly according to claim 1, wherein the sealing means comprise at least a plug at least partially made of a material selected from the group comprising rubbers, thermoplastic elastomers, and any combination and analogs thereof.

7. Needle assembly according to claim 6, wherein the material is an olefin based thermoplastic elastomer.

8. Needle assembly according to claim 1, wherein the needle hub and the needle-bearing portion are at least partially made of a material selected from the group comprising rubbers, thermoplastic polymers such as polypropylene, polyethylene and any combinations and analogs thereof.

9. Needle assembly according to claim 8, wherein the needle hub and the needle bearing portion are made of polypropylene.

10. Needle assembly according to claim 1, wherein the sealing means and the needle hub, including the needle-bearing portion, are physically linked to each other so as to avoid any leakage of product in-between their respective interfaces.

11. Needle assembly according to claim 10, wherein the sealing means and the needle hub, including the needle-bearing portion, are coinjected parts.

12. Needle assembly according to claim 1, wherein said breakable portion and said sealing means are combined.

13. Needle assembly according to claim 1, wherein said engaging means and said sealing means are combined.

14. Needle assembly according to claim 1, wherein said sealing means are made of a material with a water permeation rate inferior or equal to 3 g·mm/m2·day at room temperature, measured according to the procedure "A" of the ASTM norm designation E96-93.

15. Needle assembly according to claim 1, wherein:
at least said breakable portion is designed to be distally movable by said piston at the end of an injection stroke, and
said needle assembly comprises severing means oriented toward said breakable portion and designed to be fixedly positioned compared to said needle-bearing portion in the exposed position, and arranged to break said breakable portion when it moves distally and then to allow proximal displacement of needle-bearing portion.

16. Needle assembly according to claim 15, wherein the severing means comprise at least cutting surfaces designed at the proximal end of a sleeve receiving part of the needle-bearing portion of said needle hub.

17. Needle assembly according to claim 1, wherein said engaging means comprise a radial wall portion designed to be snapped in an annular groove at least partly formed on said barrel, in the exposed position.

18. Needle assembly according to claim 17, wherein said radial wall portion is made of a deformable material.

19. Needle assembly according to claim 17, wherein said radial wall portion is a flange defined on the needle hub.

20. Needle assembly according to claim 17, wherein said radial wall portion is a plurality of radial projections defined on the needle hub.

21. Needle assembly according to claim 20, wherein the radial projections form the distal ends, the proximal ends or both ends of a plurality of longitudinal flexible legs extending respectively in the distal or the proximal direction.

22. Needle assembly according to claim 1, wherein the sealing means comprise a longitudinal skirt extending in the distal direction, said skirt receiving part of the proximal region of the needle hub and being fixedly received in the distal end of the barrel.

23. Needle assembly according to claim 22, wherein said skirt is able to fold back on itself from the exposed position to an activation position.

24. Needle assembly according to claim 1, wherein said needle assembly further comprises urging means placed between said engaging means and said needle bearing portion and designed to tend to move said needle-bearing portion apart from said engaging means in the proximal direction.

25. Needle assembly according to claim 1, wherein said needle assembly further comprises a nose designed to be adapted at the distal end of the barrel and to receive, at least in the exposed position, said needle-bearing portion, said breakable portion and said sealing means.

26. Needle assembly according to claim 1, wherein said needle assembly further comprises a needle.

27. Needle assembly according to claim 1, wherein said needle assembly further comprises a needle cover.

28. Injection device of a product comprising at least a storing device and characterized in that it comprises a needle assembly according to claim 1.

29. Injection device according to claim 28 wherein said storing device comprises at least:

a barrel of substantially tubular shape having a distal end and a proximal end, said barrel defining a chamber for receiving said product,
a piston intended to expel said product through the distal end under a distal force exerted on said piston, said storing device being prefillable with said product and said piston sealing the proximal end of said barrel.

30. Injection device according to claim 29, wherein said piston is a self standing piston.

31. Injection device according to claim 29, wherein the barrel comprises an annular groove defining on its inner wall an abutment designed to receive said radial wall portion provided on the needle-bearing portion at least in the exposed position.

32. Injection device according to claim 31, wherein the abutment is an annular ridge.

33. Injection device according to claim 29, wherein said barrel is made of a material selected from the group comprising polypropylene, polycycloolefins, and combinations thereof.

34. Injection device according to claim 29, wherein the injection device further comprises driven means for causing said piston to move toward the distal end of said needle assembly and realize the injection of the product.

35. Injection device according to claim 34, wherein said driven means comprise a hollow plunger rod designed to receive at least said needle in its retracted position.

36. Injection device according to claim 35, wherein the distal end of said plunger rod is at least partially open.

37. Injection device according to claim 35, wherein:
at least said breakable portion is designed to be distally movable by said piston at the end of an injection stroke, and
said needle assembly comprises severing means oriented toward said breakable portion and designed to be fixedly positioned compared to said needle-bearing portion in the exposed position, and arranged to break said breakable portion when it moves distally and then to allow proximal displacement of needle-bearing portion.

38. Injection device according to claim 37, wherein the distal end of said plunger rod comprises supporting means, designed to form a radial bearing surface for the piston to prevent said piston from deforming itself in said plunger rod as the severing means cut said piston under the effect of the distal force exerted on said plunger rod at the end of injection.

39. Injection device according to claim 38, wherein the supporting means comprise a radial wall portion.

40. Injection device according to claim 39, wherein the radial wall portion defines a plurality of radial extensions.

41. Needle assembly according to claim 1, wherein said sealing means are made of a material with a water permeation rate inferior or equal to 1 g·mm/m2·day at room temperature, measured according to the procedure "A" of the ASTM norm designation E96-93.

42. Needle assembly according to claim 1, wherein said sealing means are made of a material with a water permeation rate inferior or equal to 0.5 g·mm/m2·day at room temperature, measured according to the procedure "A" of the ASTM norm designation E96-93.

* * * * *